(12) United States Patent
Gould et al.

(10) Patent No.: US 12,714,809 B2
(45) **Date of Patent: *Aug. 25, 2026**

(54) METHODS AND APPARATUSES FOR CONCENTRATE VAPORIZATION

(71) Applicant: Pax Labs, Inc., San Francisco, CA (US)

(72) Inventors: Alexander J. Gould, Portola Valley, CA (US); Adam Bowen, San Mateo, CA (US); Ariel Atkins, San Francisco, CA (US); Kevin Lomeli, San Francisco, CA (US)

(73) Assignee: Pax Labs, Inc., San Francisco, CA (US)

( * ) Notice: Subject to any disclaimer, the term of this patent is extended or adjusted under 35 U.S.C. 154(b) by 235 days.

This patent is subject to a terminal disclaimer.

(21) Appl. No.: 18/599,790

(22) Filed: Mar. 8, 2024

(65) Prior Publication Data

US 2024/0382704 A1 Nov. 21, 2024

Related U.S. Application Data

(63) Continuation of application No. 16/844,497, filed on Apr. 9, 2020, now Pat. No. 11,951,249, which is a (Continued)

(51) Int. Cl.

| | |
|---|---|
| ***A61M 15/06*** | (2006.01) |
| ***A24F 40/20*** | (2020.01) |
| ***A24F 40/42*** | (2020.01) |
| ***A24F 40/50*** | (2020.01) |
| ***A24F 40/60*** | (2020.01) |
| ***A61M 11/00*** | (2006.01) |
| ***A61M 11/04*** | (2006.01) |
| ***A61M 15/00*** | (2006.01) |

(52) U.S. Cl.
CPC ............. *A61M 15/06* (2013.01); *A24F 40/42* (2020.01); *A24F 40/50* (2020.01); *A24F 40/60* (2020.01);
(Continued)

(58) Field of Classification Search
CPC .. A61M 15/06; A61M 15/0021; A61M 11/00; A61M 11/042; A24F 40/20; A24F 40/42
See application file for complete search history.

(56) References Cited

U.S. PATENT DOCUMENTS 2,443,417 A * 6/1948 Duncan ................ A61M 11/041 126/374.1
2,522,718 A * 9/1950 Huck .................. A61M 11/041 99/317

(Continued)

FOREIGN PATENT DOCUMENTS

WO WO-2007024130 A1 * 3/2007 .......... A61M 11/041

*Primary Examiner* — Kathryn E Ditmer
(74) *Attorney, Agent, or Firm* — FisherBroyles, LLP

(57) ABSTRACT

An apparatus for vaporizing a concentrate and/or a non-concentrate material is provided. The apparatus can include a housing, a reservoir, a vessel, and a heating element. The reservoir can be coupled to a lid of the apparatus and configured to hold the concentrate. The vessel can be disposed at least partially inside of the housing and can be configured to receive the reservoir when the lid of the apparatus is in a closed position with respect to the housing. The heating element can be configured to generate heat for heating the vessel, thereby vaporizing the concentrate in the reservoir to form an aerosol. Coupling the reservoir to the lid of the apparatus can enable the apparatus to be used for vaporizing the concentrate while decoupling the reservoir from the lid of the apparatus can enable the apparatus to be used for vaporizing the non-concentrate material. Related methods are also provided.

12 Claims, 12 Drawing Sheets

Related U.S. Application Data continuation of application No. 15/663,687, filed on Jul. 28, 2017, now Pat. No. 10,617,834, which is a continuation of application No. 29/572,802, filed on Jul. 29, 2016, now Pat. No. Des. 854,238.

(60) Provisional application No. 62/372,241, filed on Aug. 8, 2016.

(52) U.S. Cl.
CPC .......... *A61M 11/00* (2013.01); *A61M 11/041* (2013.01); *A61M 11/042* (2014.02); *A61M 15/0021* (2014.02); *A24F 40/20* (2020.01); *A61M 2205/3368* (2013.01)

(56) References Cited

U.S. PATENT DOCUMENTS 2,542,529 A * 2/1951 Hunt .................... A61M 11/041 392/335
2,616,024 A * 10/1952 Laibow ............... A01M 1/2077 422/305
6,285,829 B1 * 9/2001 Smith ................ F24D 19/0082 392/347
9,399,080 B2 * 7/2016 Irvin ...................... A61L 9/032
10,462,849 B1 * 10/2019 Reichert ................ A24F 40/42
10,517,331 B2 * 12/2019 Atkins ................ A24B 15/302
2009/0293892 A1 * 12/2009 Williams ............... A24F 40/42 131/194
2009/0302019 A1 * 12/2009 Selenski ................ A24F 40/50 219/482
2012/0255546 A1 * 10/2012 Goetz ................. A61M 11/042 128/202.21
2015/0257447 A1 * 9/2015 Sullivan ............... A61M 15/06 131/329
2016/0165954 A1 * 6/2016 Hovespian ........... A24F 40/485 131/329
2016/0227836 A1 * 8/2016 Starkenburg ........... A24F 40/42
2016/0331912 A1 * 11/2016 Trzecieski .......... A61M 11/042
2016/0331913 A1 * 11/2016 Bourque .......... A61M 15/0098
2017/0156403 A1 * 6/2017 Gill ...................... A24F 40/465
2018/0352858 A1 * 12/2018 Rojo-Calderon ...... H05B 6/108

* cited by examiner

METHODS AND APPARATUSES FOR CONCENTRATE VAPORIZATION

RELATED APPLICATION

This application is a continuation of U.S. patent application Ser. No. 16/844,497 filed Apr. 9, 2020, now U.S. Pat. No. 11,951,249, entitled "METHODS AND APPARATUSES FOR CONCENTRATE VAPORIZATION," which is a continuation of U.S. patent application Ser. No. 15/663,687 filed Jul. 28, 2017, now U.S. Pat. No. 10,617,834, entitled "METHODS AND APPARATUSES FOR CONCENTRATE VAPORIZATION," which claims priority to U.S. Design application Ser. No. 29/572,802 filed Jul. 29, 2016, now U.S. Design Pat. No. D854,238, entitled "COVER FOR A VAPORIZER DEVICE," and U.S. Provisional Application No. 62/372,241 filed Aug. 8, 2016, entitled "CONCENTRATE VAPORIZING SYSTEMS". The disclosures of which are incorporated herein by reference in their entirety.

TECHNICAL FIELD

This disclosure relates generally to vaporizer apparatuses, and more specifically to methods and apparatuses for concentrate vaporization.

BACKGROUND

Electronic inhalable aerosol apparatuses, which are commonly referred to as vaporizer apparatuses, vaporization apparatuses, electronic vaping apparatuses, and/or the like, are configured to heat a vaporizable material to generate an aerosol vapor capable of delivering an active ingredient to a user.

Dabbing refers to a method of consuming concentrated doses of *Cannabis*. *Cannabis* concentrate is typically formed by extracting tetrahydrocannabinol (THC) and/or other cannabinoids using a solvent such as, for example, butane, carbon dioxide, and/or the like. The extraction process yields an often sticky oil commonly known as wax, shatter, budder, and/or butane hash oil (BHO). One common approach to vaporizing these substances involves taking a portion (e.g., a bolus, a dab, and/or the like) of the *Cannabis* concentrate, heating it on a high temperature element, commonly known as a nail, and then inhaling the resulting vapor through a dab rig.

SUMMARY

Methods, and articles of manufacture, including apparatuses, are provided for concentrate vaporization. In some implementations of the current subject matter, there is provided an apparatus for vaporizing a concentrate. The apparatus can include a housing, a reservoir, a vessel, and a heating element. The reservoir can be coupled to a lid of the apparatus. The reservoir can be configured to hold a concentrate. The vessel can be disposed at least partially inside of the housing. The vessel can be configured to receive the reservoir when the lid of the apparatus is in a closed position with respect to the housing. The heating element can be configured to generate heat for heating the vessel. The heating of the vessel can vaporize the concentrate in the reservoir to form an aerosol.

Implementations of the current subject matter can include, but are not limited to, methods and apparatuses consistent with the descriptions provided herein. The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes, it should be readily understood that such features are not intended to be limiting. The claims that follow this disclosure are intended to define the scope of the protected subject matter.

BRIEF DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings.

When practical, similar reference numbers denote similar structures, features, or elements.

DETAILED DESCRIPTION

Figure 1A:
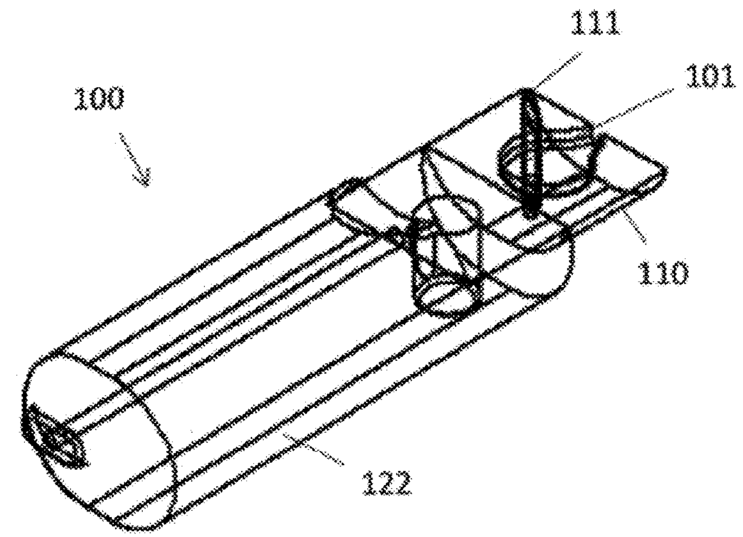
FIG. 1A depicts a perspective view of a vaporizer including a wand adaptor consistent with some implementations of the current subject matter.

Concentrates can be vaporized to deliver a more potent dose of active ingredients than is feasible via other delivery methods including, for example, combustion and/or vaporization of a non-concentrate material such as dry herbs and/or solutions. As such, concentrates are able to provide more effective and immediate relief for patients suffering from ailments such as, for example, pain, nausea, stress, appetite loss, insomnia, and/or the like. However, the use of concentrates, such as dabbing, typically requires cumbersome equipment. For instance, a conventional system for vaporizing concentrates includes a high temperature element (e.g., a nail), a pipe that is compatible for use with the high temperature element, a blowtorch for heating the high temperature element, and a wand for applying a portion (e.g., a bolus, a dab, and/or the like) of the concentrate to the high temperature element. Furthermore, proper use of this conventional system for vaporizing concentrates requires precise timing and dexterity. For example, a user must know relatively precisely when and how to apply the concentrate to the high temperature element in order for the concentrate to vaporize properly. Various implementations of the current subject matter may provide advantages relative to existing approaches including, for example, a vaporizer capable of vaporizing concentrates that is both portable and resistant to user error. Furthermore, the vaporizer may be configured to vaporize both concentrates and non-concentrate materials such as, for example, dried herbs, solutions, and/or the like.

In some implementations of the current subject matter, the vaporizer can include a lid that covers at least a vessel within a housing of the vaporizer. The vaporizer can further include a heating element, such as a hot plate and/or an oven, capable of elevating the temperature within the vessel to, for example, a level and/or a range that is suitable for vaporizing a concentrate and/or a non-concentrate material (e.g., dried herbs, solutions, and/or the like). According to some implementations of the current subject matter, the lid of the vaporizer can be configured to accept one or more permanent and/or temporary adaptors that enable the vaporization of the concentrate. For example, the lid of the vaporizer can be configured to accept an adaptor that includes a wand. A portion (e.g., a bolus, a dab, and/or the like) of concentrate can be applied to a tip of the wand. Meanwhile, the vaporizer can be configured to heat and vaporize the concentrate when the concentrate at the tip of the wand is lowered into the vessel, for example, by closing and/or fitting the lid over at least the portion of the housing of the vaporizer that includes the vessel. Alternately and/or additionally, the lid of the vaporizer can be configured to accept an adaptor that includes a reservoir for holding one or more portions (e.g., boluses, dabs, and/or the like) of a concentrate. The vaporizer can heat and vaporize the concentrate when the reservoir is deposited within the vessel, for example, by closing and/or fitting the lid over at least the portion of the housing of the vaporizer that includes the vessel.

As used herein, the term "*Cannabis*" can refer to plants of the genus *Cannabis* as well as loose-leaf products and/or extracts thereof. Meanwhile, the term "cannabinoid" can refer to plant-based and/or synthetic chemical compounds capable of acting upon cannabinoid receptors and/or inducing a biological effect. Cannabinoids include acids, salts, bioactive stereo isomers, and/or the like. For example, cannabinoids can include tetrahydrocannabinol (THC), cannabigerolic acid (CBGA), cannabigerol (CBG), tetrahydrocannabinolic acid (THCA), cannabichromene (CBC), cannabicyclol (CBL), cannabivarin (CBV), cannabichromevarin (CBCV), cannabigerovarin (CBGV), cannabigerol Monomethyl Ether (CBGM), delta-8-tetrahydrocannabinol (D8THC), delta-9-tetrahydrocannabinol (D9THC), tetrahydrocannabivarin (THCV), cannabinolic acid (CBNA), Cannabinol (CBN), cannabidiolic acid (CBDA), Cannabidivaric acid (CBDVA), cannabidiol (CBD), cannabichromenic acid (CBCA), Cannabichromene (CBC), or cannabicyclolic acid (CBLA) and/or any salt or stereo isomer of the above. For clarity and conciseness, various implementations of the current subject matter are described with respect to *Cannabis* concentrates and/or concentrates containing one or more cannabinoids as an active ingredient. However, it should be appreciated that various implementations of the current subject matter are also applicable to concentrates containing different and/or additional active ingredients including, for example, botanicals, pharmaceuticals, nutraceutical, synthetically-derived similar substances and/or the like.

Figure 1B:
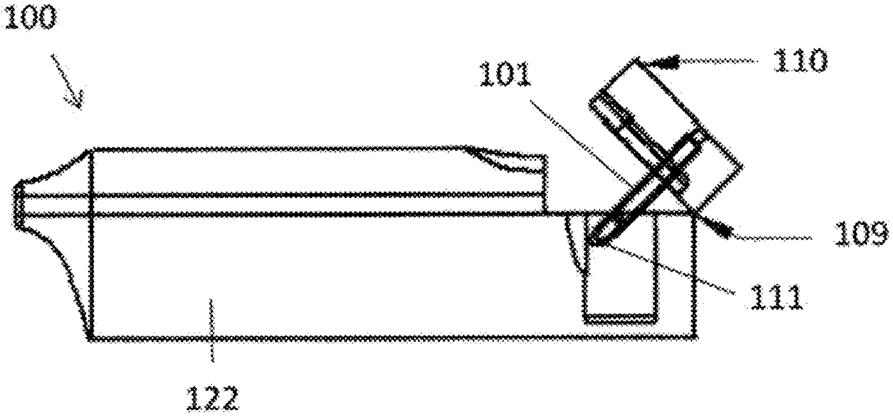
FIG. 1B depicts a lateral cross section view of a vaporizer including a wand adaptor consistent with some implementations of the current subject matter.
Figure 1C:
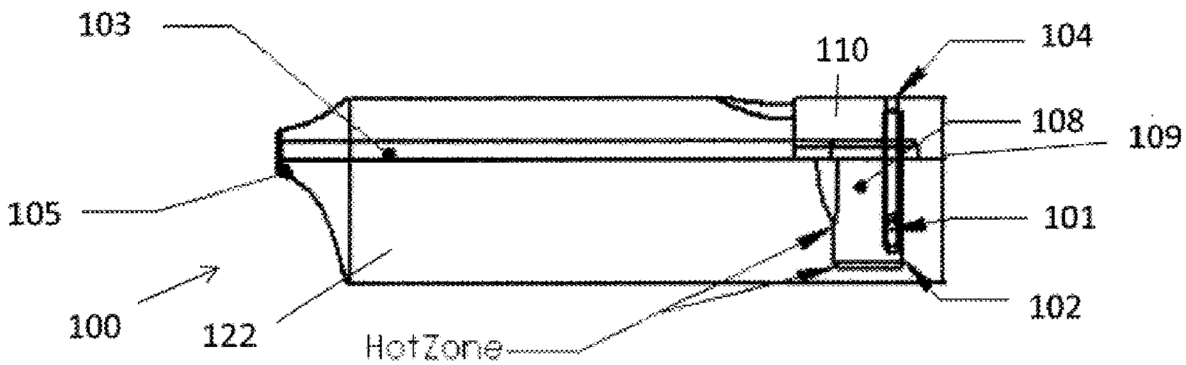
FIG. 1C depicts a lateral cross section view of a vaporizer including a wand adaptor consistent with some implementations of the current subject matter.

FIGS. 1A-C depict a vaporizer 100 including a wand adaptor consistent with some implementations of the current subject matter. Referring to FIGS. 1A-C, the vaporizer 100 can include a vessel 102, which can be disposed within a cavity at one end of a housing 122 of the vaporizer 100. As shown in FIGS. 1A-C, the vaporizer 100 can be an elongated cylinder having an oval cross-section. However, it should be appreciated that the vaporizer 100 can be configured to have any shape, dimension, and/or contour.

In the vaporizer 100 shown in FIGS. 1A-C, the vessel 102 can be oriented such that the open top of the vessel 102 is parallel to the sides of the housing 122. The vaporizer 100 can further include a lid 110 configured to cover at least a portion of the housing 122. The lid 110 can be a flip-lid that pivots around a hinge 109 in order to transition between an open position and a closed position with respect to the housing 122. However, it should be appreciated that the lid 110 can be fully detachable from the housing 122. The lid 110 and/or the housing 122 can include one or more mechanisms, such as snaps, latches, grooves, threading, magnets, clips, quick connect, sliding mechanisms, quarter turn release, friction fit, and/or the like, configured to position and/or secure the lid 110 against the housing 122 when, for example, the lid 110 is in the closed position. As shown in FIG. 1C, when the lid 110 is in the closed position, the lid 110 can cover and/or otherwise enclose the vessel 102 and/or the cavity within the housing 122 containing the vessel 102 to form an air chamber 108. Although not shown, the lid 110 and/or the housing 122 can include an air gap and/or thermal insulation material configured to maintain a temperature within the vaporizer 100, for example, when the vaporizer 100 is in use. The thermal insulation material may be, for example, rubbers (e.g., silicone, silicone foam, polyurethane foam, and/or the like), aerogel, fiberglass insulators, and/or the like.

To use the vaporizer 100 for vaporizing a non-concentrate material such as dry herbs, a portion of the non-concentrate material can be placed directly into the vessel 102. Alternately and/or additionally, a wand adaptor can be added to the vaporizer 100 in order to enable the vaporizing of a concentrate such as, for example, a *Cannabis* concentrate and/or the like. Thus, in some implementations of the current subject matter, the lid 110 can be configured to receive, as a permanent and/or a temporary attachment, a wand adaptor that includes a wand 101. The wand adaptor can be attached to the lid 110 using one or more mechanisms including, for example, snaps, latches, grooves, threading, magnets, clips, quick connect, sliding mechanisms, quarter turn release, friction fit, and/or the like. Furthermore, the wand 101 can be a hollow tube formed from any material capable of withstanding and/or retaining heat including, for example, metals (e.g., aluminum (Al)), metal alloys (e.g., stainless steel), ceramics, and/or the like. As can be seen in FIGS. 1A-C, when the wand adaptor is attached to the lid 110, the hollow center of the wand 101 can be aligned with an aperture 104 in the lid 110, thereby forming an air passage through the lid 110 and the wand 101. A tip 111 of the wand 101 can be beveled and/or otherwise shaped to facilitate the application of a concentrate, such as a bolus or a dab of *Cannabis* concentrate, to the tip 111 of the wand 101. Closing the lid 110 against the housing 122 can lower the concentrate at the tip 111 of the wand 101 into the vessel 102.

The vessel 102 can be any hollow, open-top receptacle such as, for example, a crucible and/or the like. Moreover, the vessel 102 can be formed from any material, such as, for example, metals (e.g., aluminum (Al)), metal alloys (e.g., stainless steel), ceramics, and/or the like, that is capable of tolerating high temperatures and/or retaining heat. Although not shown, the vaporizer 100 can include one or more electric (e.g., battery) powered heating elements capable of generating heat for elevating the temperature within the vessel 102 to, for example, an appropriate level and/or range for vaporizing a concentrate. Once the lid 110 is closed and the concentrate at the tip 111 of the wand 101 is lowered into the vessel 102, the elevated temperature within the vessel 102 and/or the air chamber 108 can lower the viscosity of the concentrate, thereby causing the concentrate to loosen from the tip 111 of the wand 101 and drip onto an interior surface of the vessel 102. A user inhaling from a mouthpiece 105 at an opposite end of the housing 122 from the vessel 102 can cause an intake of air through the aperture 104 and the hollow center of the wand 101. The resulting air flow can further loosen the concentrate from the tip 111 of the wand 101. Upon contact with the heated interior surface of the vessel 102, the concentrate can rapidly vaporize and mix with additional air in the air chamber 108 to form an aerosol. This aerosol can travel down an air path 103 through the housing 122 and exit from the vaporizer 100 through the mouthpiece 105. It should be appreciated that the mouthpiece 105 can be configured to enable the user to draw, for example via inhalation, the aerosol from the vaporizer 100.

In some implementations of the current subject matter, the vaporizer 100 can include a temperature control system for adjusting the target temperature for heating the vessel 102. For example, the target temperature for the vessel 102 may be set lower (e.g., between 220° C. and 240° C.) when the vaporizer 100 is being used to gradually vaporize the concentrate and/or to maximize the flavor of the resulting aerosol. By contrast, the target temperature of the vessel 102 may be set higher (e.g., greater than 400° C.) in order to vaporize the concentrate immediately and maximize the dose of the active ingredient that is delivered at once. The vaporizer 400 can further include one or more visual, audio, and/or motion indicators, such as light-emitting diodes (LEDs), along the housing 122 and/or the lid 110. These indicators can be used to indicate, for example, the current temperature within the vessel 102, the target temperature for the vessel 102, and/or when the aerosol has been formed.

Although the vaporizer 100 is shown to include a wand adaptor including the wand 101, it should be appreciated that the vaporizer 100 can also be compatible with different and/or additional adaptors, such as a reservoir adaptor, that enables the vaporizer 100 to be used for vaporizing a concentrate. For example, in some implementations of the current subject matter, the lid 110 can be configured to receive a plurality of interchangeable adaptors including, for example, a wand adaptor, a reservoir adaptor, and/or the like.

Figure 2A:
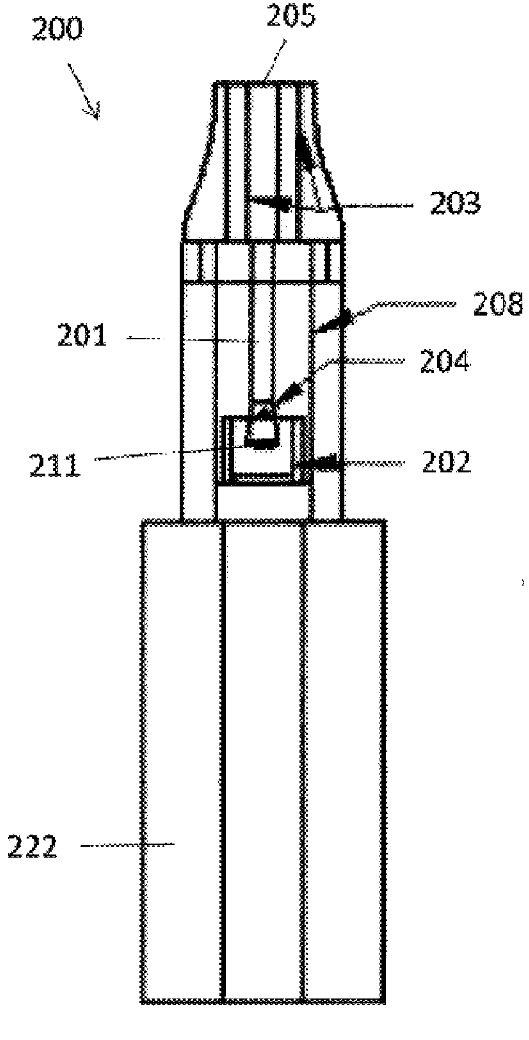
FIG. 2A depicts a perspective view of a vaporizer including a wand adaptor consistent with some implementations of the current subject matter.
Figure 2B:
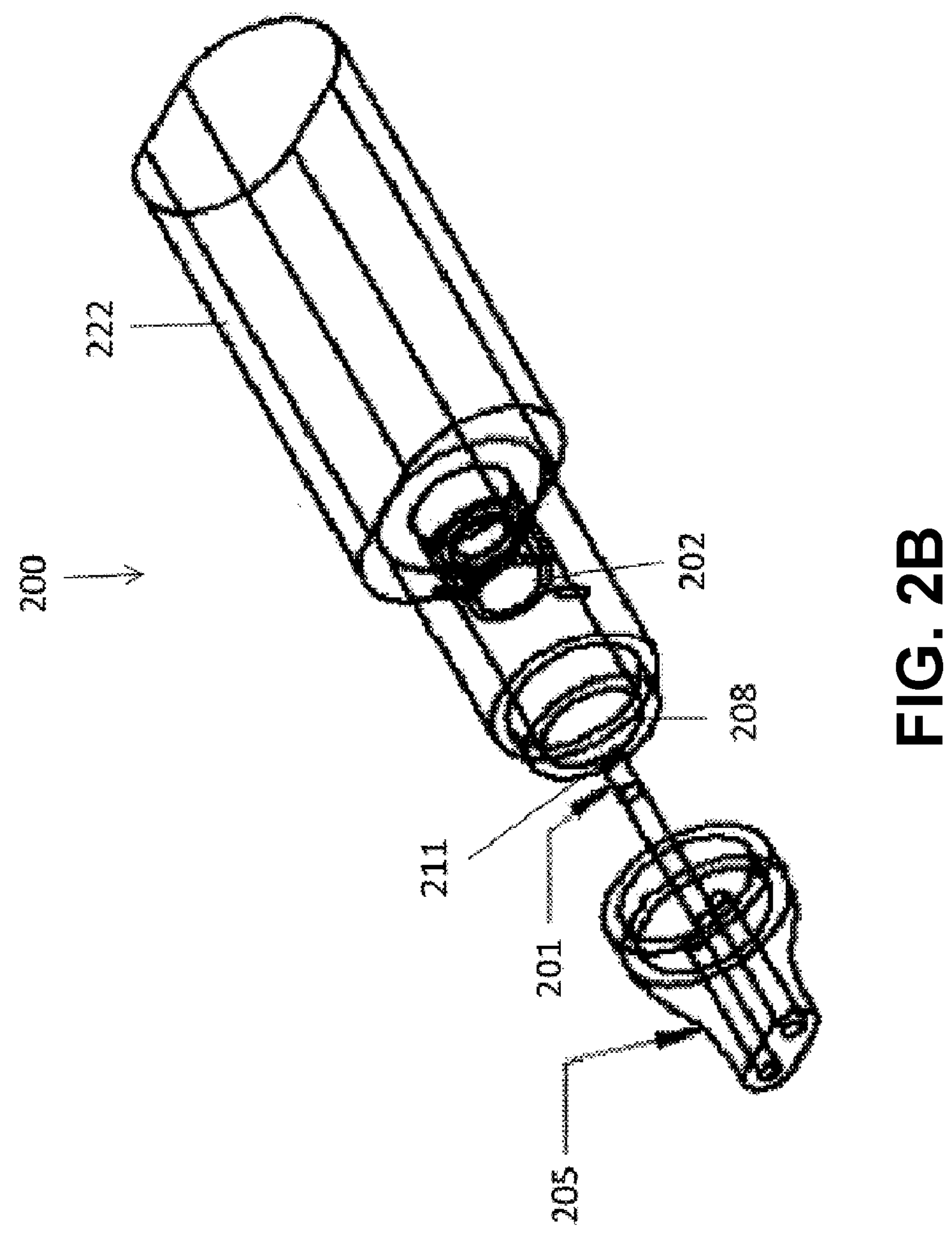
FIG. 2B depicts a lateral cross section view of a vaporizer including a wand adaptor consistent with some implementations of the current subject matter.

FIG. 2A-B depicts a vaporizer 200 consistent with some implementations of the current subject matter. Referring to FIG. 2A-B, the vaporizer 200 can include a vessel 202, which can be disposed within a cavity at one end of a housing 222 of the vaporizer 200. As shown in FIGS. 2A-B, the vaporizer 200 can be an elongated cylinder having an oval cross-section. However, it should be appreciated that the vaporizer 200 can be configured to have any shape, dimension, and/or contour.

In the vaporizer 200, the vessel 202 can be oriented such that the open top of the vessel 202 is perpendicular to the sides of the housing 222 and parallel to the ends of the housing 222. The vaporizer 200 can further include a mouthpiece 205 having one or more air paths 203. As shown in FIGS. 2A-B, the mouthpiece 205 can be coupled to one end of the housing 222. The mouthpiece 205 can be removable such that the mouthpiece 205 is fully and/or partially detached from a housing 222 of the vaporizer 200. Furthermore, the mouthpiece 205 can cover and/or otherwise enclose the vessel 202 and/or the cavity within the housing 222 containing the vessel 202 to form an air chamber 208. The mouthpiece 205 and/or the housing 222 can include one or more mechanisms, such as snaps, latches, grooves, threading, magnets, clips, quick connect, sliding mechanisms, quarter turn release, friction fit, and/or the like, configured to position and/or secure the mouthpiece 205 against the housing 222 when, for example, the mouthpiece 205 is attached to the housing 222. Although not shown, the mouthpiece 205 and/or the housing 222 can include thermal insulation material configured to maintain a temperature within the vaporizer 200, for example, when the vaporizer 200 is in use.

To use the vaporizer 200 for vaporizing a non-concentrate material such as dry herbs, a portion of the non-concentrate material can be placed directly into the vessel 202. Alternately and/or additionally, a wand adaptor can be added to the vaporizer 200 in order to enable the vaporizing of a concentrate such as, for example, a *Cannabis* concentrate and/or the like. Thus, in some implementations of the current subject matter, the mouthpiece 205 can be configured to receive, as a permanent and/or a temporary attachment, a wand adaptor that includes a wand 201. For example, the wand adaptor can be attached to the mouthpiece 205 using one or more mechanisms including, for example, snaps, latches, grooves, threading, magnets, clips, quick connect, sliding mechanisms, quarter turn release, friction fit, and/or the like. The wand 201 can be a hollow tube formed from any material capable of withstanding and/or retaining heat including, for example, metals (e.g., aluminum (Al)), metal alloys (e.g., stainless steel), ceramics, and/or the like. When the wand adaptor is attached to the mouthpiece 205, the hollow center of the wand 201 can be aligned with the air paths 203 in the mouthpiece 205, thereby forming an air passage through the mouthpiece 205 and the wand 201. A tip 211 of the wand 201 can be beveled and/or other shaped to facilitate the application of a concentrate, such as a bolus or a dab of *Cannabis* concentrate, to the tip 211 of the wand 201. Attaching the mouthpiece 205 to the housing 222 can lower the concentrate at the tip 211 of the wand 201 into the vessel 202.

The vessel 202 can be any hollow, open-top receptacle such as, for example, a crucible and/or the like. Moreover, the vessel 202 can be formed from any material, such as, for example, metals (e.g., aluminum (Al)), metal alloys (e.g., stainless steel), ceramics, and/or the like, that is capable of tolerating high temperatures and/or retaining heat. Although not shown, the vaporizer 200 can include one or more electric (e.g., battery) powered heating elements that generates the heat for elevating the temperature within the vessel 202 to, for example, an appropriate level and/or range for vaporizing a concentrate. When the mouthpiece 205 is attached to the housing 222 and the concentrate at the tip 211 of the wand 201 is lowered into the vessel 202, the elevated temperature within the vessel 202 and/or the air chamber 208 can lower the viscosity of the concentrate, thereby causing the concentrate to loosen from the tip 211 of the wand 201 and drip onto an interior surface of the vessel 202. A user inhaling from the mouthpiece 205 can cause an intake of air through the air paths 203 in the mouthpiece 205 and the hollow center of the wand 201. The resulting air flow, which can enter and/or exit from an aperture 204 in at and/or proximate to the tip 211, can further loosen the concentrate from the tip 211. Upon contact with the heated interior surface of the vessel 202, the concentrate can rapidly vaporize and mix with additional air in the air chamber 208 to form an aerosol. This aerosol can exit from the vaporizer 100 through the air paths 203 in the mouthpiece 205. It should be appreciated that the mouthpiece 105 can be configured to enable the user to draw, for example via inhalation, the aerosol from the vaporizer 200.

In some implementations of the current subject matter, the vaporizer 200 can include a temperature control system for adjusting the target temperature for heating the vessel 202. For example, the target temperature for the vessel 202 may be set lower (e.g., between 220° C. and 240° C.) when the vaporizer 200 is being used to gradually vaporize the concentrate and/or to maximize the flavor of the resulting aerosol. By contrast, the target temperature of the vessel 202 may be set higher (e.g., greater than 400° C.) in order to vaporize the concentrate immediately and maximize the dose of the active ingredient that is delivered at once. The vaporizer 200 can further include one or more visual, audio, and/or motion indicators, such as light-emitting diodes (LEDs), along the mouthpiece 205 and/or the housing 222. These indicators can be used to indicate, for example, the current temperature within the vessel 202, the target temperature for the vessel 202, and/or when the aerosol has been formed.

Although the vaporizer 200 is shown to include a wand adaptor including the wand 201, it should be appreciated that the vaporizer 200 can also be compatible with different and/or additional adaptors, such as a reservoir adaptor, that enables the vaporizer 200 to be used for vaporizing a concentrate. For example, in some implementations of the current subject matter, the mouthpiece 205 can be configured to receive a plurality of interchangeable adaptors including, for example, a wand adaptor, a reservoir adaptor, and/or the like.

Figure 3A:
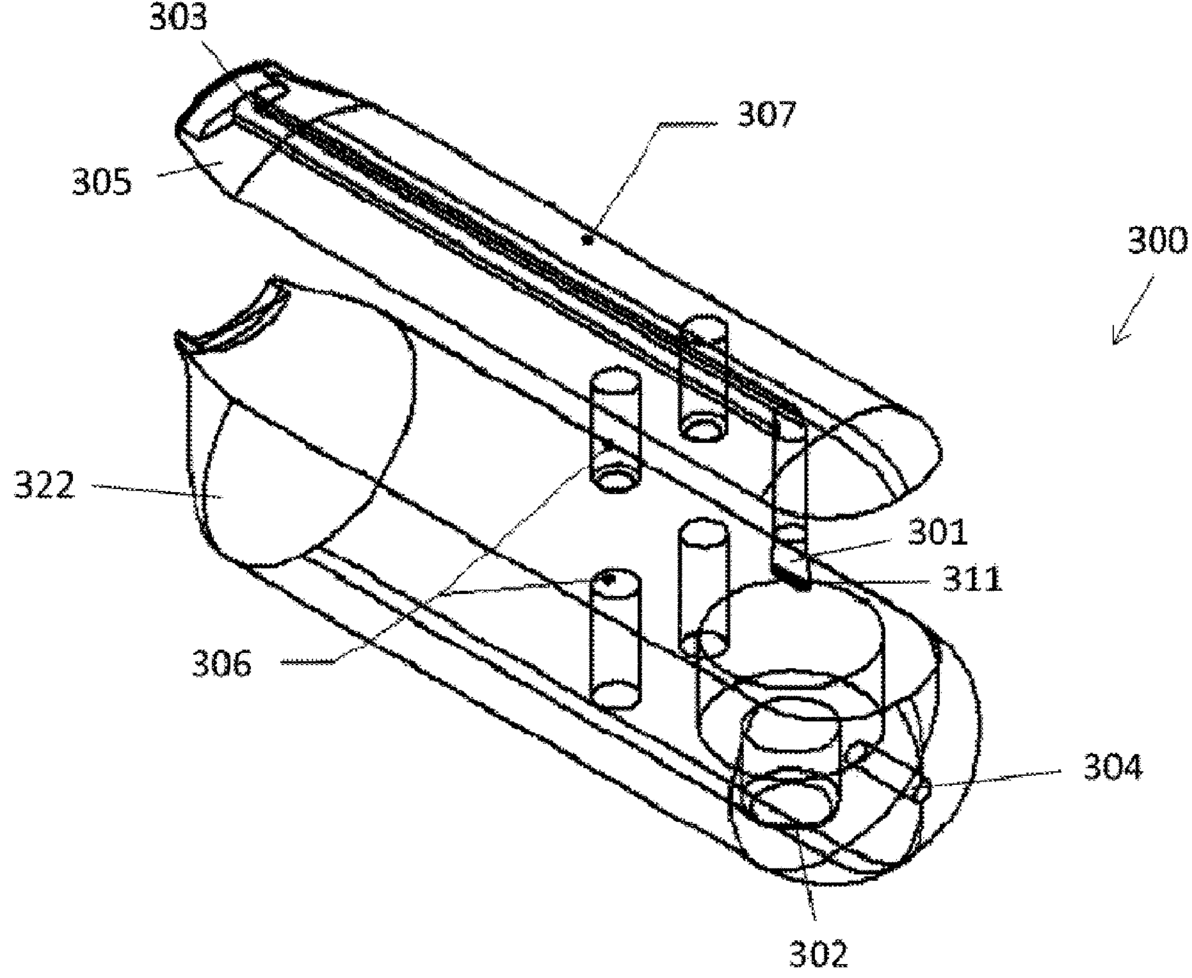
FIG. 3A depicts a perspective view of a vaporizer including a wand adaptor consistent with some implementations of the current subject matter.
Figure 3B:
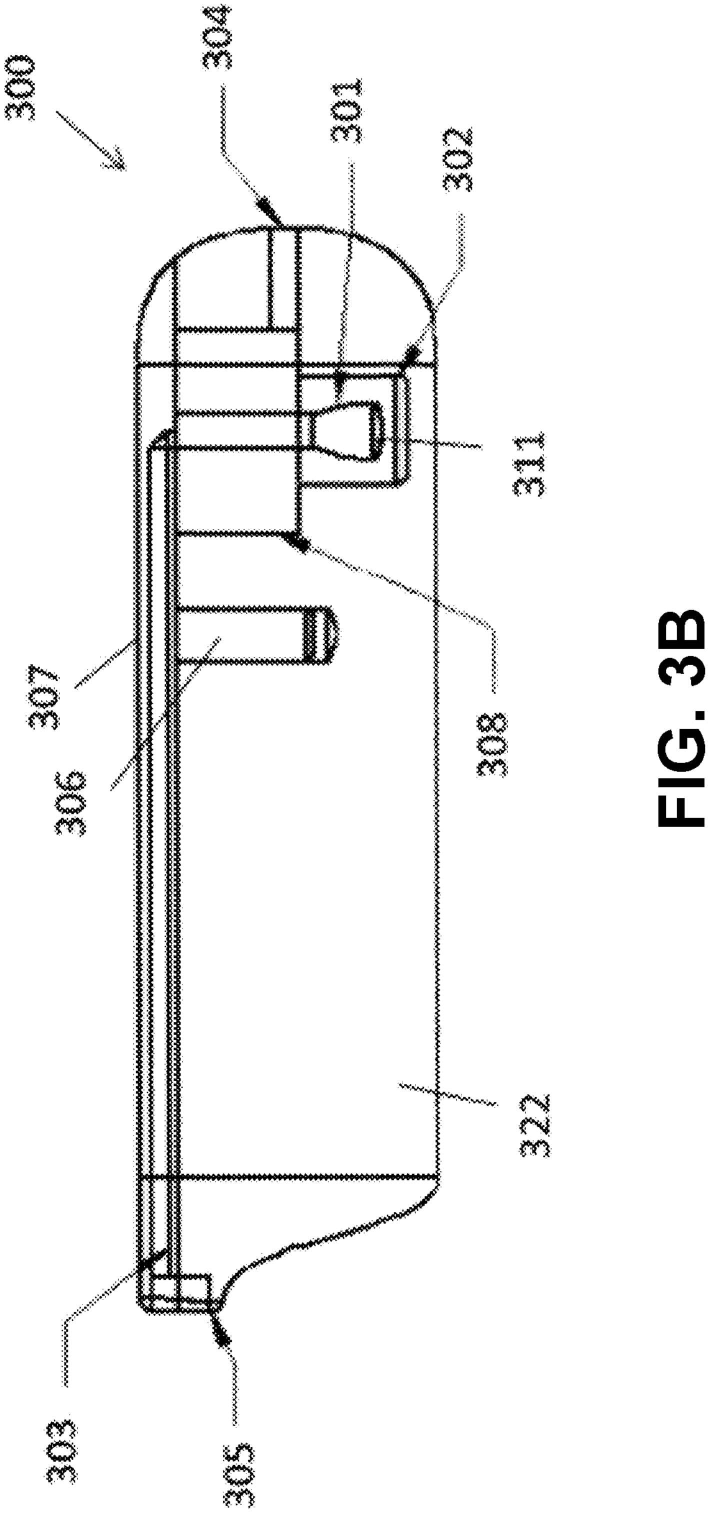
FIG. 3B depicts a lateral cross section view of a vaporizer including a wand adaptor consistent with some implementations of the current subject matter.

FIGS. 3A-B depict a vaporizer 300 consistent with some implementations of the current subject matter. Referring to FIGS. 3A-B, the vaporizer 300 can include a vessel 302, which can be disposed within a cavity at one end of a housing 322 of the vaporizer 300. In the vaporizer 300 shown in FIGS. 3A-B, the vessel 302 can be oriented such that the open top of the vessel 302 is parallel to the sides of the housing 322. Furthermore, the vaporizer 300 can include a cover 307, which extends along a length of the housing 322. As shown in FIGS. 1A-C, the cover 307 can be coupled with the housing 322 to form an elongated cylinder having an oval cross-section. However, it should be appreciated that the vaporizer 300 can be configured to have any shape, dimension, and/or contour.

The cover 307 can be fully and/or partially detached from the housing 322. Moreover, the cover 307 and/or the housing 322 can include one or more alignment features 306 configured to position and/or orient the cover 307 with respect to the housing 322. As shown in FIGS. 3A-B, the alignment features 306 can include one or more protrusions such as, for example, pins, prongs, and/or the like, that extends from the cover 307. The alignment features 306 can further include corresponding recesses within the housing 322 configured to receive the prongs extending from the cover 307 when, for example, the cover 307 is in a closed position over the housing 322. Alternatively and/or additionally, the cover 307 and/or the housing 322 can include one or more mechanisms, such as snaps, latches, grooves, threading, magnets, clips, quick connect, sliding mechanisms, quarter turn release, friction fit, and/or the like, can be used to position and/or secure the cover 307 against the housing 322 when, for example, the cover 307 is in the closed position over the housing 322. It should be appreciated that when the cover 307 is in the closed position, the cover 307 can cover and/or otherwise enclose the vessel 302 and/or the cavity within the housing 322 containing the vessel 302 to form an air chamber 308. Furthermore, although not shown, the cover 307 and/or the housing 322 can include thermal insulation material configured to maintain a temperature within the vaporizer 300, for example, when the vaporizer 300 is in use.

To use the vaporizer 300 for vaporizing a non-concentrate material such as dry herbs, a portion of the non-concentrate material can be placed directly into the vessel 302. Alternately and/or additionally, a wand adaptor can be added to the vaporizer 300 in order to enable the vaporizing of a concentrate such as, for example, a *Cannabis* concentrate and/or the like. Thus, in some implementations of the current subject matter, the cover 307 can be configured receive, as a permanent and/or a temporary attachment, a wand adaptor that includes a wand 301. For example, the wand adaptor can be attached to the cover 307 using one or more mechanisms including, for example, snaps, latches, grooves, threading, magnets, clips, quick connect, sliding mechanisms, quarter turn release, friction fit, and/or the like. The wand 301 can be a hollow tube formed from any material capable of withstanding and/or retaining heat including, for example, metals (e.g., aluminum (Al)), metal alloys (e.g., stainless steel), ceramics, and/or the like. As shown in FIGS. 3A-B, the cover 307 can further include a mouthpiece 305, which can be disposed at an opposite end of the cover 307 away from the wand adaptor. An air path 303 can extend from the wand 301 to the mouthpiece 305. For instance, one open end of the air path 303 can be coupled with the mouthpiece 305. Meanwhile, when the wand adaptor is attached to the cover 307, the hollow center of the wand 301 can be aligned with the other open end of the air path 303. An aperture 304 can be disposed at an opposite end of the housing 322 away from the mouthpiece 305. The aperture 304 can provide an opening into the vessel 302 and/or the cavity within the housing 322 containing the vessel 302, thereby allowing air to enter into the air chamber 308 when the vaporizer 300 is in use.

According to some implementations of the current subject matter, a tip 311 of the wand 301 can be beveled and/or otherwise shaped to facilitate the application of a concentrate, such as a bolus or a dab of *Cannabis* concentrate, to the tip 311 of the wand 301. Closing the cover 307 over the housing 322 can lower the concentrate at the tip 311 of the wand 301 into the vessel 302. It should be appreciated that the vessel 302 can be any hollow, open-top receptacle such as, for example, a crucible and/or the like. Moreover, the vessel 302 can be formed from any material such as, for example, metals (e.g., aluminum (Al)), metal alloys (e.g., stainless steel), ceramics, and/or the like, that is capable of tolerating high temperatures and/or retaining heat. Although not shown, the vaporizer 300 can include one or more electric (e.g., battery) powered heating elements that generates the heat for elevating the temperature within the vessel 302 to, for example, an appropriate level and/or range for vaporizing a concentrate.

Once the cover 307 is closed over the housing 322 and the concentrate at the tip 311 of the wand 301 is lowered into the vessel 302, the elevated temperature within the vessel 302 and/or the air chamber 308 can lower the viscosity of the concentrate, thereby causing the concentrate to loosen from the tip 311 of the wand 301 and drip onto an interior surface of the vessel 302. A user inhaling from the mouthpiece 305 can cause an intake of air. For example, the inhalation can cause air to enter the air chamber 308 through the aperture 304 and travel through air path 303 to the mouthpiece 305. The resulting air flow can further loosen the concentrate from the tip 311 of the wand 301. In either of these ways, with the concentrate contacting the heated interior surface of the vessel 302, it can rapidly vaporize and mix with additional air in the air chamber 308 to form an aerosol. This aerosol can also travel down the air path 303 through the cover 307 and exit from the vaporizer 300 through the mouthpiece 305. It should be appreciated that the mouthpiece 305 can be configured to enable the user to draw, for example via inhalation, the aerosol from the vaporizer 300.

In some implementations of the current subject matter, the vaporizer 300 can include a temperature control system for adjusting the target temperature for heating the vessel 302. For example, the target temperature for the vessel 302 may be set lower (e.g., between 220° C. and 240° C.) when the vaporizer 300 is being used to gradually vaporize the concentrate and/or to maximize the flavor of the resulting aerosol. By contrast, the target temperature of the vessel 302 may be set higher (e.g., greater than 400° C.) in order to vaporize the concentrate immediately and maximize the dose of the active ingredient that is delivered at once The vaporizer 400 can further include one or more visual, audio, and/or motion indicators, such as light-emitting diodes (LEDs), along the cover 307 and/or the housing 322. These indicators can be used to indicate, for example, the current temperature within the vessel 302, the target temperature for the vessel 302, and/or when the aerosol has been formed.

Although the vaporizer 300 is shown to include a wand adaptor including the wand 101, it should be appreciated that the vaporizer 300 can also be compatible with different and/or additional adaptors, such as a reservoir adaptor, that enables the vaporizer 300 to be used for vaporizing a concentrate. For example, in some implementations of the current subject matter, the cover 307 can be configured to receive a plurality of interchangeable adaptors including, for example, a wand adaptor, a reservoir adaptor, and/or the like.

Figure 4A:
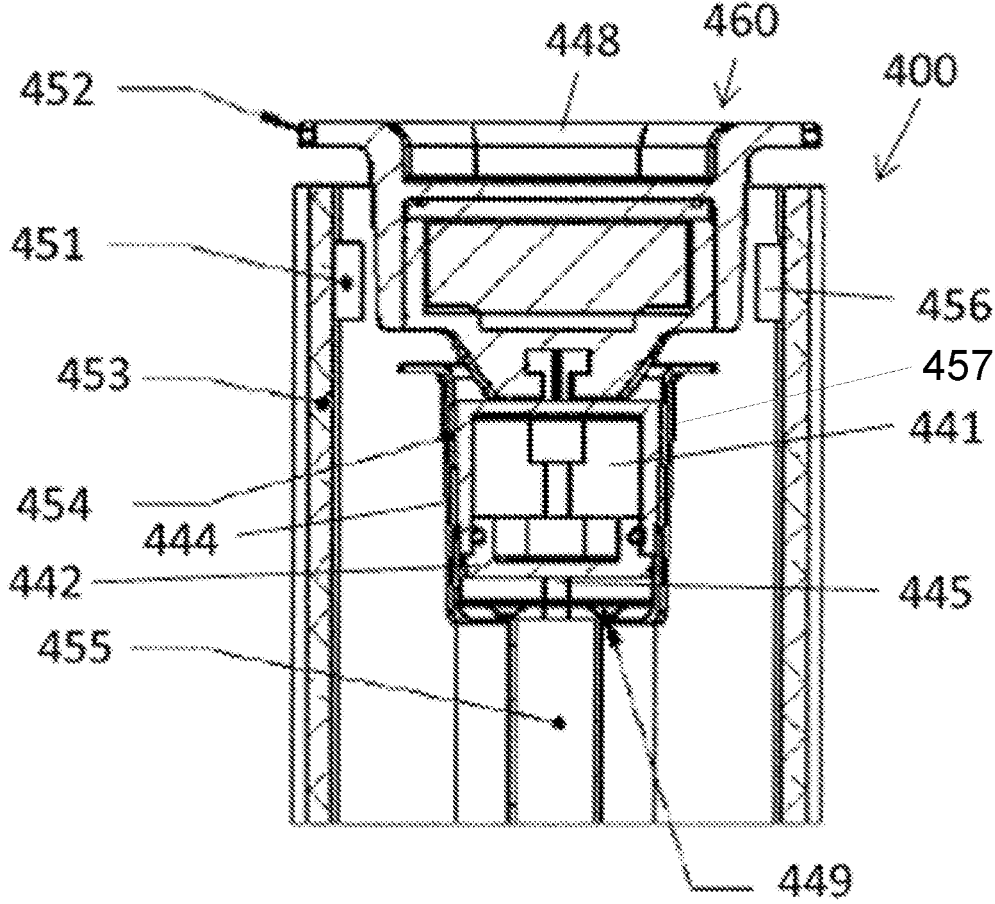
FIG. 4A depicts a cross section view of a vaporizer including a lid assembly consistent with some implementations of the current subject matter.
Figure 4B:
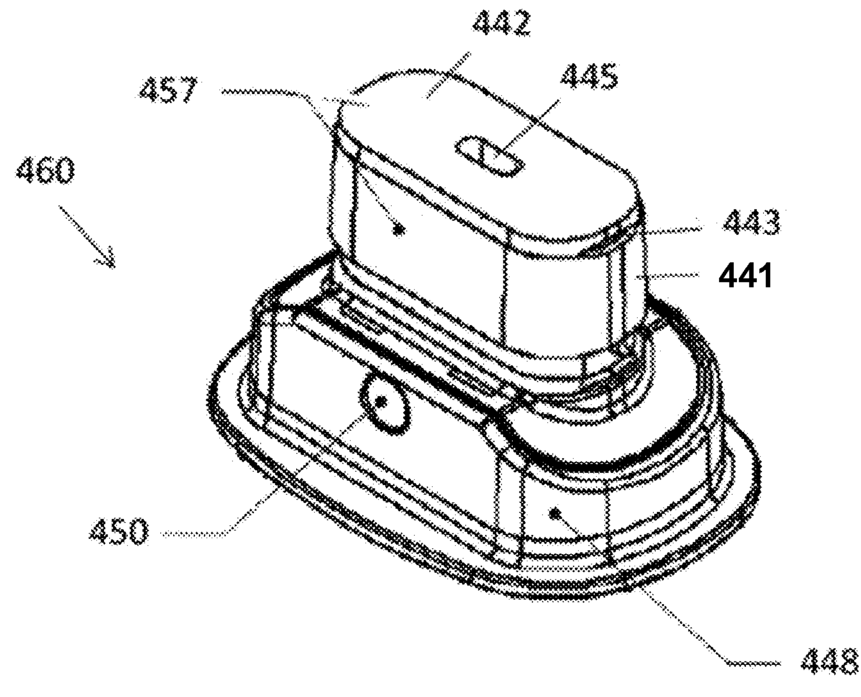
FIG. 4B depicts a perspective view of a lid assembly consistent with some implementations of the current subject matter.
Figure 4C:
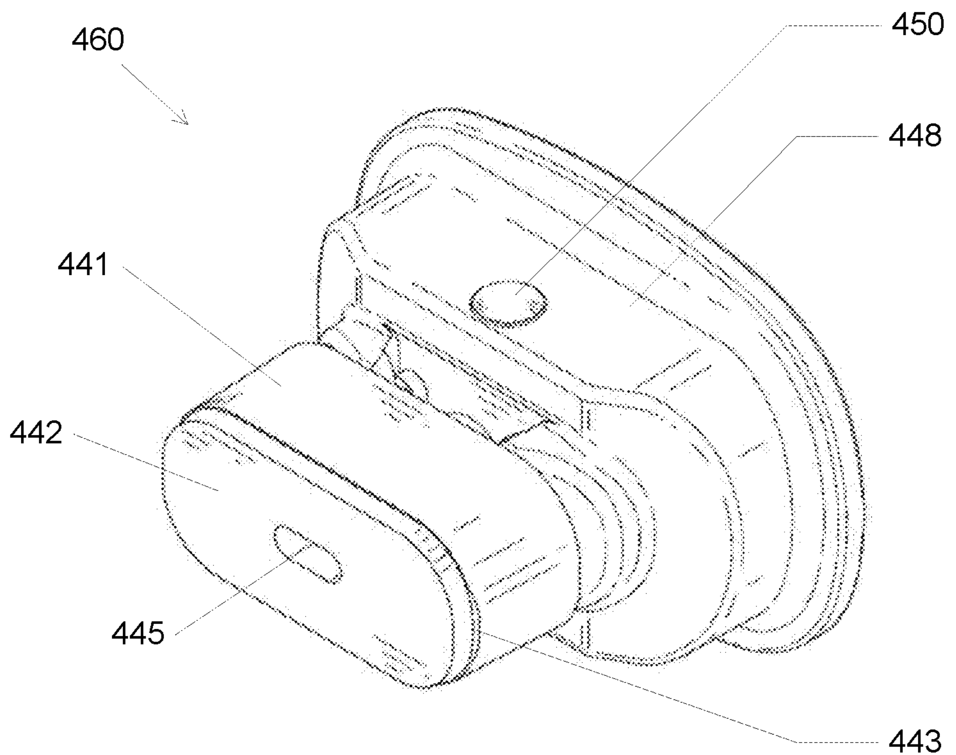
FIG. 4C depicts a perspective view of a lid assembly consistent with some implementations of the current subject matter.
Figure 4D:
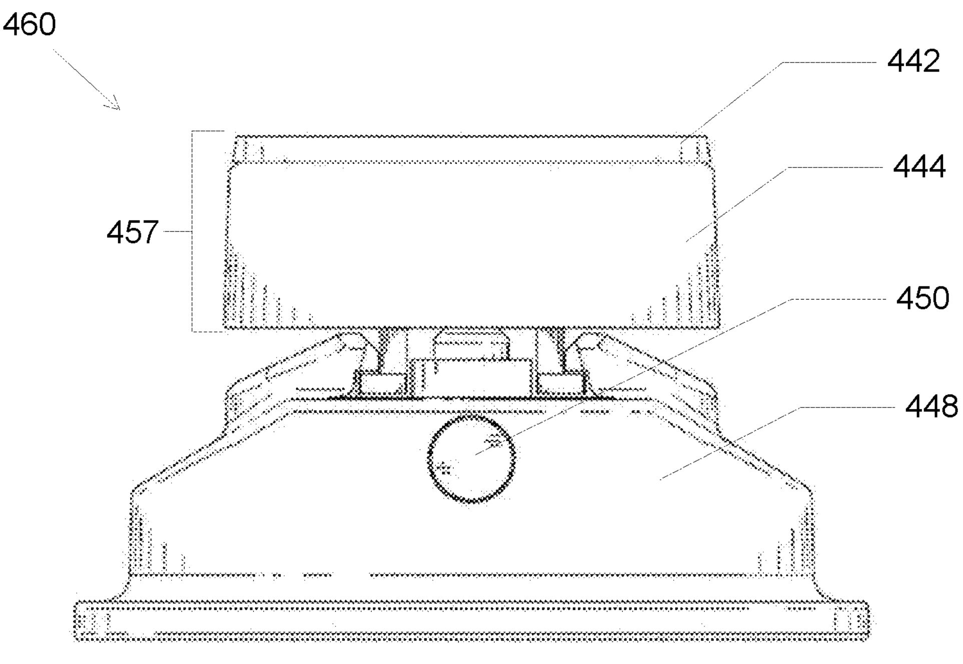
FIG. 4D depicts a side view of a lid assembly consistent with some implementations of the current subject matter.
Figure 4E:
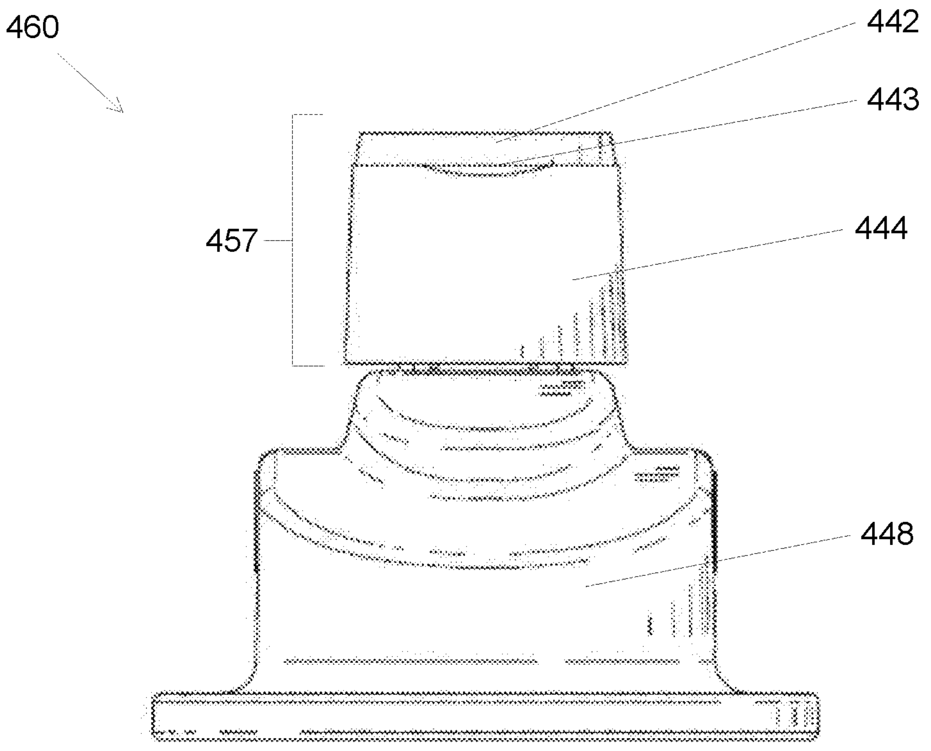
FIG. 4E depicts a side view of a lid assembly consistent with some implementations of the current subject matter.
Figure 4F:
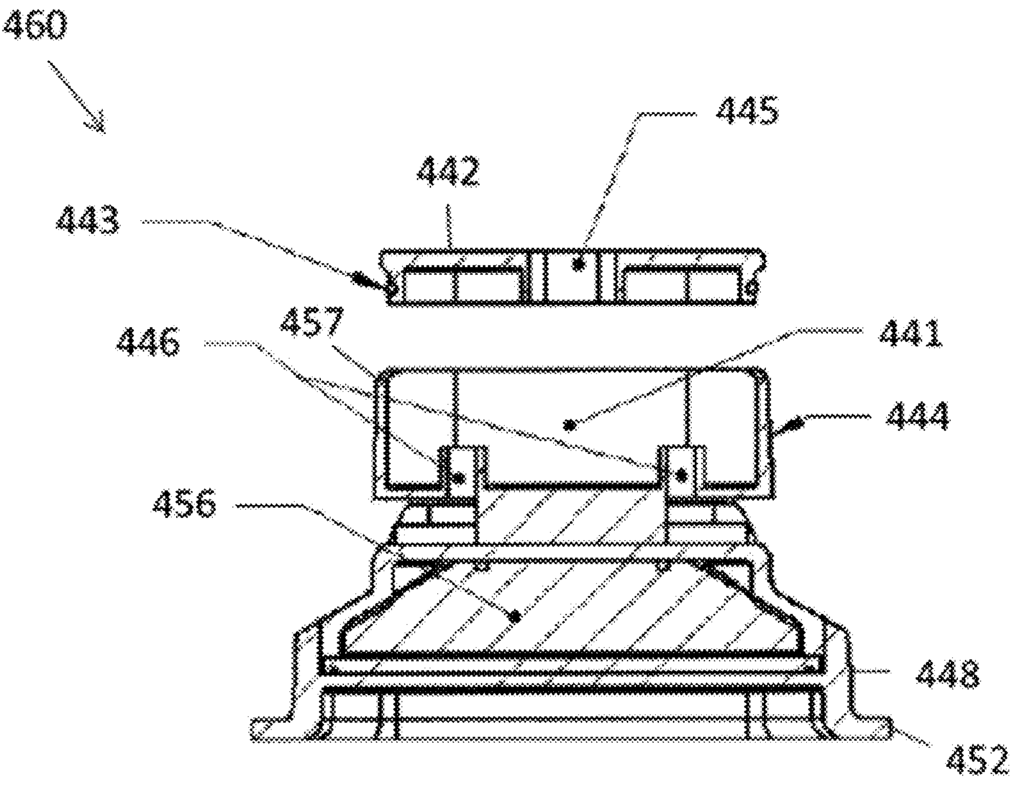
FIG. 4F depicts a cross section view of a lid assembly consistent with some implementations of the current subject matter.
Figure 4G:
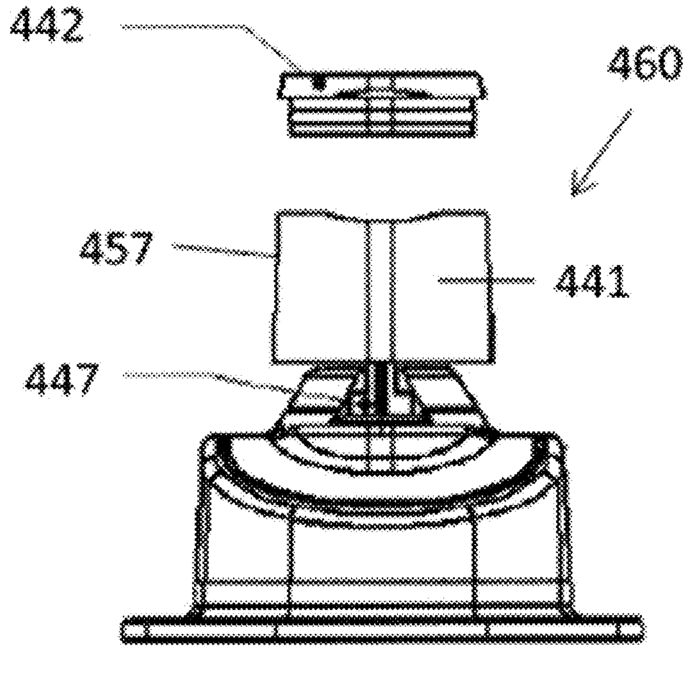
FIG. 4G depicts a cross section view of a lid assembly consistent with some implementations of the current subject matter.

FIG. 4A depicts a cross view of a vaporizer 400 consistent with some implementations of the current subject matter. Referring to FIG. 4A, the vaporizer 400 can include a vessel 454, which can be disposed at one end of the vaporizer 400, for example, within a housing 453 of the vaporizer 400. In the vaporizer 400 shown in FIG. 4A, the vessel 454 can be oriented such that the open top of the vessel 454 is perpendicular to the sides of the housing 453 and parallel to an open top at one end of the housing 453. It should be appreciated that the vaporizer 400 can be configured to have any shape, dimension, and/or contour including, for example, an elongated cylinder having an oval, circular, and/or rectangular cross section.

In some implementations of the current subject matter, the vaporizer 400 can further include a lid 448 configured to cover the open top at one end of the housing 453. Meanwhile, a mouthpiece (not shown) may be at the opposite end of the housing 453. The lid 448 and/or the housing 453 can include one or more locking mechanisms, such as snaps, latches, grooves, threading, magnets, clips, quick connect, sliding mechanisms, quarter turn release, friction fit, and/or the like, configured to position and/or secure the lid 448 when, for example, the lid 448 is in the closed position against the housing 453. For example, as shown in FIGS. 4A-G, the lid 448 can include one or more magnets 450 while the housing 453 can include one or more additional magnets 451 for securing the lid 448 in place when the lid 448 is in the closed position. A perimeter around a top edge of the lid 448 can be fully and/or partially surrounded by a flange 452. The flange 452 can be a projecting rim, collar, rib, and/or the like configured to facilitate the attachment and/or removal of lid 448 from the housing 453 of the vaporizer 400. Furthermore, the lid 448 and/or the housing 453 can include thermal insulation material 456 configured to maintain a temperature within the vaporizer 400 when the vaporizer 400 is in use.

To use the vaporizer 400 for vaporizing a non-concentrate material such as dry herbs, a portion of the non-concentrate material can be placed directly into the vessel 454. In some implementations of the current subject matter, a screen 449 can sit at a bottom of the vessel 454. The screen 449 can be configured to prevent extraneous material, such as loose herbs, from entering an air path 455 that extends from the vessel 454 to the mouthpiece (not shown). Alternately and/or additionally, a reservoir adaptor 457 can be added to the vaporizer 400 in order to enable the vaporization of a concentrate such as, for example, a *Cannabis* concentrate and/or the like. Thus, in some implementations of the current subject matter, the lid 448 can be configured to receive, as a permanent and/or a temporary attachment, the reservoir adaptor 457, thereby forming a lid assembly 460. For instance, as shown in FIGS. 4A-G, the lid 448 and/or the reservoir adaptor 457 can include one or more retention features 447, such as snaps, latches, grooves, threading, magnets, clips, quick connect, sliding mechanisms, quarter turn release, friction fit, and/or the like, configured to releasably attach the reservoir adaptor 457 to the lid 448.

FIG. 4B-G depicts the lid assembly 460 consistent with some implementations of the current subject matter. Referring to FIGS. 4A-G, the lid assembly 460 can include the lid 448 of the vaporizer 400 and the reservoir adaptor 457. The reservoir adaptor 457 can include a reservoir 441 and a cover 442. The reservoir 441 and/or the cover 442 can be formed from material capable of withstanding and/or retaining heat including, for example, metals (e.g., aluminum (Al)), metal alloys (e.g., stainless steel), ceramics, and/or the like. The cover 442 can be configured to couple with an open top of the reservoir 441 to form an enclosed space for holding a concentrate. In some implementations of the current subject matter, the cover 442 can include a seal 443 for securing the cover 442 to the reservoir 441. The seal 443 can be, for example, a gasket (e.g., O-ring) formed from one or more elastomers such as, for example, perfluoroelastomer, silicone, and/or the like. However, it should be appreciated that the cover 442 can be secured to the reservoir 441 using a different and/or additional mechanism including, for example, snaps, latches, grooves, threading, magnets, clips, quick connect, sliding mechanisms, quarter turn release, friction fit, and/or the like.

As noted, the reservoir 441 can be configured to hold a concentrate such as, for example, wax, shatter, budder, butane hash oil, and/or the like. For example, a user can load the concentrate into the reservoir 441 before covering and/or sealing the reservoir 441 with the cover 442 and/or the seal 443. It should be appreciated that the reservoir 441 may be configured to hold a larger quantity (e.g., multiple portions) of the concentrate than can be applied to the tip of a wand. Once the reservoir 441 is loaded with the concentrate and covered and/or sealed with the cover 442 and/or the seal 443, the user can insert the lid assembly 460 into the vaporizer 400 and/or close the lid 448 against the housing 453. Doing so can deposit the covered and/or sealed reservoir 441 into the vessel 454. According to some implementations of the current subject matter, an exterior surface 444 of the reservoir 441 can be configured to conform to the dimensions, shapes, and/or contours of an interior surface of the vessel 454. For instance, the exterior surface 444 of the reservoir 441 can be tapered in order to match a tapering of the interior surface of the vessel 454. This conformation between the exterior surface 444 of the reservoir 441 and the interior surface of the vessel 454 can maximize contact between the reservoir 441 and the vessel 454 when the reservoir 441 is disposed within the vessel 454.

Although not shown, the vaporizer 400 can include one or more electric (e.g., battery) powered heating elements. These heating elements may generate heat for elevating the temperature within the vessel 454, thereby heating the reservoir 441 and the contents therein to a temperature and/or a range of temperature (e.g., 220° C.-240° C.) that is appropriate for vaporizing, for example, a concentrate such as a *Cannabis* concentrate. As noted, contact between the reservoir 441 and the vessel 454 can be maximized due to the close conformation between the respective dimensions, shapes, and/or contours of the exterior surface 444 of the reservoir 441 and the interior surface of the vessel 454. It should be appreciate heat transfer between the reservoir 441 and the vessel 454 can be maximized as a result of the maximum contact between the reservoir 441 and the vessel 454.

Referring again to FIGS. 4A-G, the lid assembly 460 can include a plurality of apertures configured to allow the passage of air. For example, the cover 442 can include a first aperture 445 configured to allow air to exit the reservoir 441. Alternately and/or additionally, the reservoir 441 can include one or more second apertures 446, which can be configured to allow air to enter into the reservoir 441 from, for example, outside of the vaporizer 400. A user inhaling from the mouthpiece (not shown) of the vaporizer 400 can cause an intake of air into the reservoir 441. For instance, the user's inhalation can draw air through the second apertures 446 and into the reservoir 441. The incoming air can mix with the vapor generated by the vaporization of the contents of the reservoir 441 to form an aerosol. Furthermore, the resulting air flow can carry the aerosol out of the reservoir

441 through the first aperture 445. The aerosol can travel through the air path 455 to the mouthpiece (not show) at the other end of the vaporizer 400 where the aerosol is delivered to the user. Although not shown, the mouthpiece can be configured to enable the user to draw, for example via inhalation, the aerosol from the vaporizer 400.

In some implementations of the current subject matter, the vaporizer 400 can include a temperature control system for adjusting the target temperature for heating the vessel 454. For example, the target temperature for the vessel 454 may be set lower (e.g., between 220° C. and 240° C.) when the vaporizer 400 is being used to gradually vaporize the concentrate and/or to maximize the flavor of the resulting aerosol. By contrast, the target temperature of the vessel 454 may be set higher (e.g., greater than 400° C.) in order to vaporize the concentrate immediately and maximize the dose of the active ingredient that is delivered at once. The vaporizer 400 can further include one or more visual, audio, and/or motion indicators, such as light-emitting diodes (LEDs), along the housing 453 and/or the lid 448. These indicators can be used to indicate, for example, the current temperature within the vessel 454, the target temperature for the vessel 454, and/or when the aerosol has been formed.

Although the vaporizer 400 is shown to include the reservoir adaptor 457, it should be appreciated that the vaporizer 400 can also be compatible with different and/or additional adaptors, such as a wand adaptor, that enables the vaporizer 400 to be used for vaporizing a concentrate. For example, in some implementations of the current subject matter, the lid 448 can be configured to receive a plurality of interchangeable adaptors including, for example, a wand adaptor, a reservoir adaptor, and/or the like.

Figure 5B:
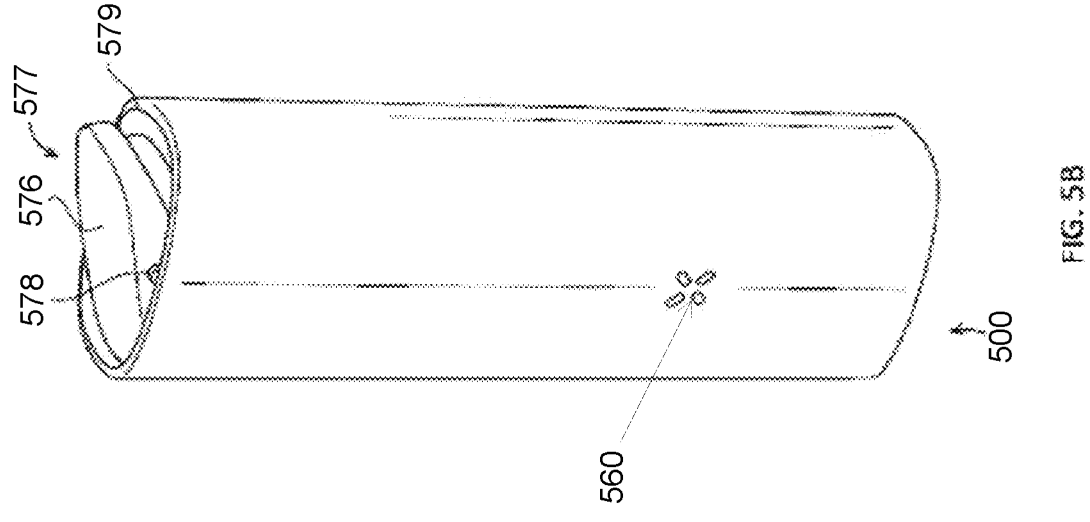
FIG. 5B depicts a perspective view of a vaporizer consistent with some implementations of the current subject matter.
Figure 5A:
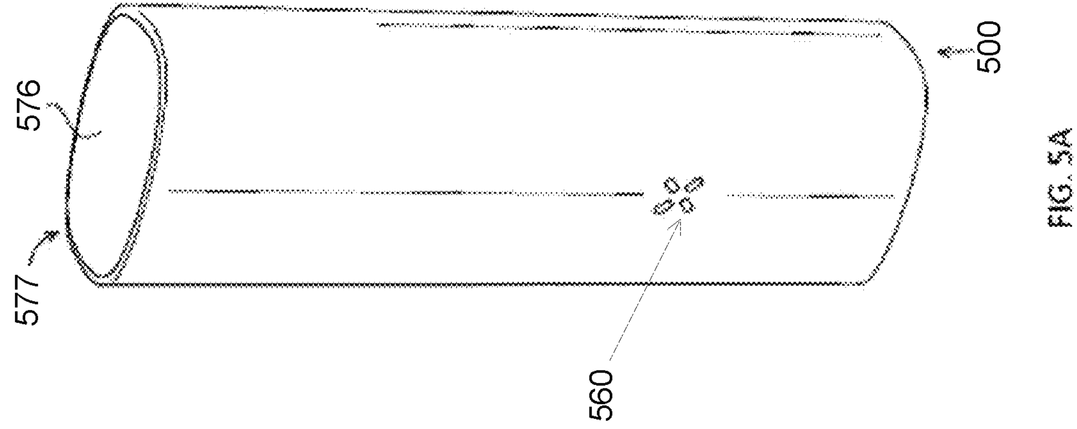
FIG. 5A depicts a perspective view of a vaporizer consistent with some implementations of the current subject matter.
Figure 5C:
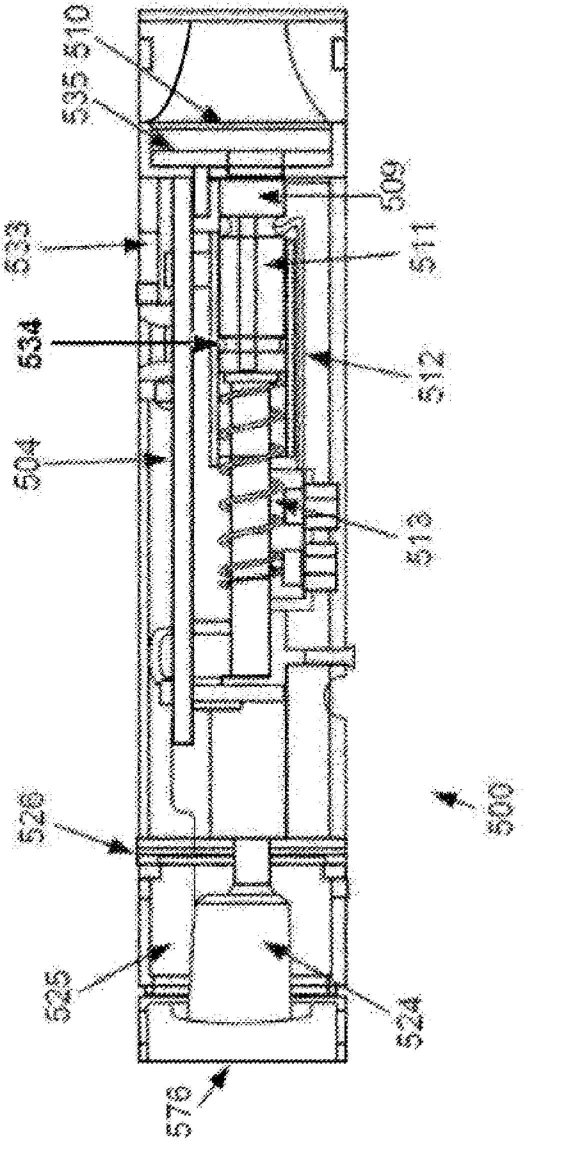
FIG. 5C depicts a cross section view of a vaporizer consistent with implementations of the current subject matter.

FIGS. 5A-C depict a vaporizer 500 consistent with some implementations of the current subject matter. As shown in FIGS. 5A-B, the vaporizer 500 can include a lid 576, which can be configured to pivot and/or swivel with respect to a hinge 578 in order to transition between an open position and a closed position. The hinge 578 can be a mechanical hinge such as, for example, a ball and socket joint, and/or the like. Alternately and/or additionally, the hinge 578 can be a magnetic hinge formed by one or more pairs of magnets embedded in the lid 576 and in the corresponding locations along a housing of the vaporizer 500. The pairs of magnets can further serve to secure the lid 576 in place when the lid 576 is in the closed position. However, it should be appreciated that the lid 576 can be secured using different and/or additional mechanisms including, for example, snaps, latches, grooves, threading, magnets, clips, quick connect, sliding mechanisms, quarter turn release, friction fit, and/or the like. For example, as shown in FIGS. 5A-B, the lid 576 can be held in place using a magnet 577 and/or a snap 579.

When the lid 576 is in the closed position, the lid 576 can be fully ensconced within the housing of the vaporizer 500. Positioning the lid 576 as such can prevent the lid 576 from being opened inadvertently, for instance, during storage and/or transportation of the vaporizer 500. According to some implementations of the current subject matter, the lid 576 can be opened by depressing one side of the lid 576. Doing so may cause the lid 576 to swivel and/or pivot around the hinge 578, thereby opening the lid 576 and exposing the interior of the vaporizer 500. It should be appreciated that any vaporizer consistent with various implementations of the current subject matter, including the vaporizer 100, the vaporizer 200, the vaporizer 300, and/or the vaporizer 400, can be implemented to include a pivoting recessed lid such as the lid 576. Furthermore, the lid 576 can be replaced with the lid assembly 460 described with respect to FIGS. 4A-G. Replacing the lid 576 with the lid assembly 460 can enable the vaporizer 500 to be used for vaporizing a concentrate such as, for example, a *Cannabis* concentrate.

Referring to FIG. 5C, the vaporizer 500 can include a deep-drawn stainless steel heating chamber 524 ("oven"), with polyimide thin film circuit heater applied. A push-push mechanism for retracting mouthpiece consists of compression spring 513, leaf spring 512, and stainless steel tube 511 attached to the mouthpiece 510, with a catch groove 534 and a toggle slider 509. Reed switch/hall effect sensor 533 is incorporated to detect if mouthpiece is inserted (device runs off). To extend the mouthpiece into the "on" position, the user presses on the mouthpiece 510. The mouthpiece is attached to the tube 511, so this action compresses the compression spring 513. This action also causes the leaf spring 512 to flex away from the axis of the tube and onto the outer diameter of the toggle slider 509. When the user then releases the mouthpiece, the compression spring pushes the mouthpiece & tube sub-assembly outward from the device. The angled lip of the leaf spring catches on the toggle slider, causing the slider to traverse the tube until it reaches a shoulder on the tube. At this point, the mouthpiece continues to extend out of the device, and the leaf spring now wipes along the toggle slider and continues along the shoulder of the outer diameter of the tube, which is of equivalent diameter and thus poses no resistance. When the catch groove of the tube intersects with the lip of the leaf spring, the mouthpiece stops, and is now in the extended, "on" position. Pressing the mouthpiece from the "on" position uses the push-push mechanism to move the mouthpiece to a retracted position. The push-push mechanism, thus, is configured to toggle the mouthpiece between an "on" position or an extended position such that the mouthpiece is extended from the body of the device, and a retracted position.

In some implementations of the current subject matter, in the retracted position, the mouthpiece is fully within the body of the device. Alternatively and/or additionally, in the retracted position, the mouthpiece is fully within the body of the device but is exposed at the open end of the device. In some implementations of the current subject matter, in the retracted position, the mouthpiece is substantially within the body of the device such that a portion of the mouthpiece extends beyond the end out of the body of the device.

In some implementations of the current subject matter, the vaporizer 500 may include a temperature regulation scheme in that the temperature regulator (bimetallic discs or other regulator) are located in close proximity to the area where temperature is most critical, for example, at the heating chamber 524. As shown in FIG. 5C, the vaporizer 500 can include a temperature select button 535, a printed circuit board 504, and an O-ring seal 526 to control potential aerogel dusting, and insulation chamber 525 to contain aerogel blanket. Furthermore, as shown in FIGS. 5A-B, the exterior of the vaporizer 500 may include one or more visual, audio, and/or motion indicators 560, such as light-emitting diodes (LEDs), for indicating the current temperature within the heating chamber 524, the target temperature for the heating chamber 524, and/or when the aerosol has been formed.

The descriptions of vaporizer apparatuses, such as for example relative and/or absolute arrangements of a body, a mouthpiece, an oven, one or more buttons, etc. provided herein are intended to provide context of possible implementations in which features of the current subject matter may be incorporated. Such descriptions should not be consulted as limiting except to the extent that they are included in the claims. For example, other configurations than those described herein and shown in the figures are within the scope of the current subject matter.

Figure 6:
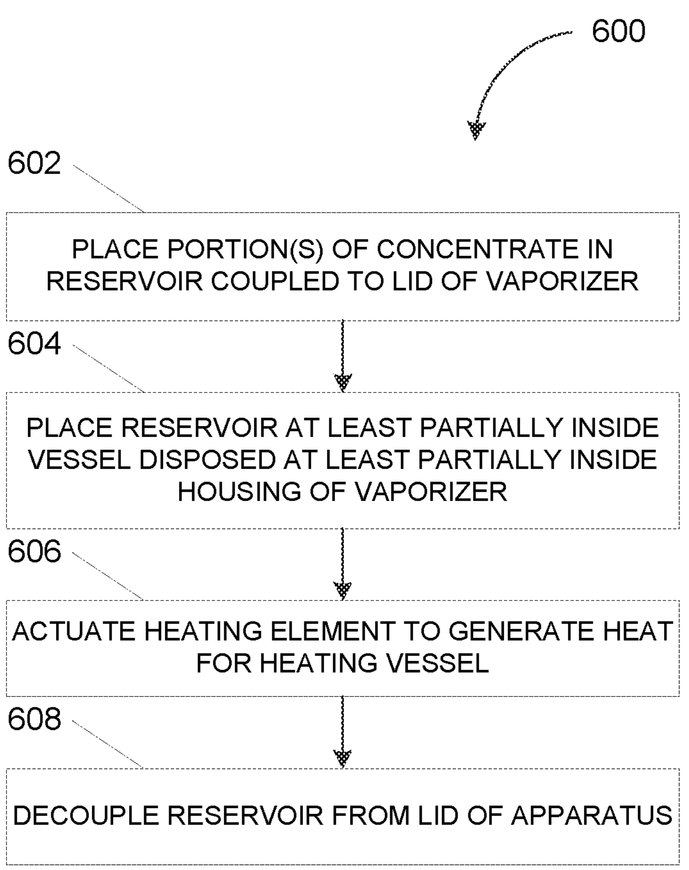
FIG. 6 depicts a flowchart illustrating a process for utilizing a vaporizer consistent with some implementations of the current subject matter.

FIG. 6 depicts a flowchart illustrating a process 600 for utilizing a vaporizer consistent with some implementations of the current subject matter. Referring to FIG. 6, the process 600 may be performed when utilizing the vaporizer 400 for vaporizing a concentrate and/or a non-concentrate material. However, it should be appreciated that the process 600 may also be performed with respect to any one of the vaporizer 100, the vaporizer 200, the vaporizer 300, or the vaporizer 500.

One or more portions of a concentrate can be placed in a reservoir coupled to a lid of a vaporizer (602). For example, a user can deposit one or more portions (e.g., boluses, dabs, and/or the like) of a concentrate (e.g., a *Cannabis* concentrate) into the reservoir 441, which can be part of the reservoir adaptor 457. As noted, the reservoir adaptor 457 can be coupled with the lid 448 of the vaporizer 400 to form the lid assembly 460.

The reservoir can be placed at least partially inside a vessel disposed at least partially inside a housing of the vaporizer (604). For instance, the reservoir 441 including the concentrate can be covered with the cover 442 and further sealed using the seal 443. The user can place the reservoir 441 inside the vessel 454 by inserting the lid assembly 460 into the vaporizer 400 and/or closing the lid 448 against the housing 453 of the vaporizer 400.

A heating element can be activated to generate heat for heating the vessel (606). In some implementations of the current subject matter, the vaporizer 400 can include a temperature control system that allows the user to set the target temperature for heating the vessel. As such, the user can set the target temperature for heating the vessel 454 to a temperature and/or a range of temperature (e.g., between 220° C. and 240° C. and/or greater than 400° C.) appropriate for vaporizing the concentrate included in the reservoir 441. Heating the vessel 454 can cause the concentrate inside the reservoir 441 to vaporize and form an aerosol that can be delivered to the user, for example, via the mouthpiece of the vaporizer 400.

The reservoir can be decoupled from the lid of the apparatus (608). In some implementations of the current subject matter, the reservoir adaptor 457 can be detached from the lid 448 of the vaporizer 400. Doing so can enable the vaporizer 400 to be used for vaporizing a non-concentrate material (e.g., dry herbs), which can be deposited directly into the vessel 454. Alternatively and/or additionally, the reservoir adaptor 457 can be detached from the lid 448 and replaced with a wand adaptor that includes a wand. Attaching the wand adaptor to the lid 448 can allow the vaporizer 400 to be used for vaporizing a concentrate. A portion (e.g., bolus, dab, and/or the like) of the concentrate can be placed at a tip of the wand and lowered into the vessel 454 by at least closing the lid 448 against the housing 453 of the vaporizer 400.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the steps or logic flow described herein in a certain order does not require the particular order stated or shown, or sequential order, to achieve desirable results. When examples are described, they are to include all types of examples encompassed by the phrases and/or terms used and are not limited to the particular examples mentioned. Other implementations may be within the scope of the following claims.

What is claimed is:

1. An apparatus for use with a vaporizer having a mouthpiece, the apparatus comprising:

a lid for the vaporizer; and a reservoir configured to hold a concentrate material, the reservoir having a first end and a second end opposite the first end, the first end being configured to couple with the lid of the vaporizer, the second end being at least partially sealed by a cover to form an enclosed space for holding the concentrate material, the cover comprising a single first aperture configured to allow an aerosol to exit from the reservoir;

wherein the reservoir is configured to be at least partially inserted within the vaporizer when the reservoir holds the concentrate material and is coupled to the lid; and wherein the reservoir is configured to be heated by a heating element of the vaporizer positioned outside of the reservoir to form the aerosol by at least vaporizing the concentrate material held within the reservoir.

2. The apparatus of claim 1, wherein the second end is configured to couple with the cover, wherein the cover includes a seal that secures the cover to the second end.

3. The apparatus of claim 2, wherein the second end of the reservoir comprises an open top, and wherein the cover defines the enclosed space for holding the concentrate material.

4. The apparatus of claim 1, wherein the reservoir coupled to the lid enables the apparatus to be used for vaporizing the concentrate material.

5. The apparatus of claim 1, wherein the reservoir is coupled to the lid via at least one of snaps, latches, grooves, threading, magnets, clips, a quick connect, a sliding mechanism, a quarter turn release, and friction fit.

6. The apparatus of claim 1, wherein the reservoir is coupled to the lid via a quarter turn release.

7. The apparatus of claim 1, wherein an exterior surface of the reservoir is tapered to match a tapering of an interior surface of the vaporizer.

8. The apparatus of claim 1, further comprising the concentrate material, wherein the concentrate material comprises one or more of cannabinoids including tetrahydrocannabinol (THC), cannabigerolic acid (CBGA), cannabigerol (CBG), tetrahydrocannabinolic acid (THCA), cannabichromene (CBC), cannabicyclol (CBL), cannabivarin (CBV), cannabichromevarin (CBCV), cannabigerovarin (CBGV), cannabigerol Monomethyl Ether (CBGM), delta-8-tetrahydrocannabinol (D8THC), delta-9-tetrahydrocannabinol (D9THC), tetrahydrocarmabivarin (THCV), cannabinolic acid (CBNA), Cannabinol (CBN), cannabidiolic acid (CBDA), Cannabidivaric acid (CBDVA), cannabidiol (CBD), cannabichromenic acid (CBCA), Cannabichromene (CBC), and and cannabicyclolic acid (CBLA).

9. The apparatus of claim 1, further comprising the concentrate material, wherein the concentrate material comprises at least one of a *Cannabis* concentrate, a botanical concentrate, a pharmaceutical concentrate, and a nutraceutical concentrate.

10. The apparatus of claim 1, wherein the reservoir further includes a second aperture configured to allow an entry of air into the reservoir.

11. The apparatus of claim 10, wherein the second aperture is configured to allow the aerosol to comprise a mixture of a vapor formed by the vaporization of the concentrate material and the air entering the reservoir.

12. The apparatus of claim 10, wherein the second aperture is positioned at the first end of the reservoir.

* * * * *